United States Patent [19]

Johnsen et al.

[11] Patent Number: 4,772,201
[45] Date of Patent: Sep. 20, 1988

[54] DENTAL MANDREL/POLISHING-WHEEL SYSTEM

[75] Inventors: James B. Johnsen, Beaverton; Hal J. Oien, Ashland, both of Oreg.

[73] Assignee: Jordco, Inc., Beaverton, Oreg.

[21] Appl. No.: 34,723

[22] Filed: Apr. 6, 1987

[51] Int. Cl.⁴ .............................................. A61C 3/06
[52] U.S. Cl. ..................................... 433/134; 433/125; 51/168
[58] Field of Search ............... 433/166, 125, 167, 142, 433/134, 165; 132/73.6, ; 51/168

[56] References Cited

U.S. PATENT DOCUMENTS

| | | | |
|---|---|---|---|
| 574,031 | 12/1896 | Hakins | 433/134 |
| 711,340 | 10/1902 | Paynter | 433/134 |
| 983,993 | 2/1911 | Graef | 51/168 |
| 2,286,292 | 6/1942 | Mall | 51/168 |
| 2,394,882 | 2/1946 | Weynand | 51/168 |
| 2,398,664 | 4/1946 | Paul | 51/168 |
| 2,637,148 | 5/1953 | Tingvatne | 51/168 |

*Primary Examiner*—John J. Wilson
*Assistant Examiner*—Adriene J. Lepiane
*Attorney, Agent, or Firm*—Kolisch, Hartwell & Dickinson

[57] ABSTRACT

A hygiene-promoting, dental mandrel/polishing-wheel system. The system includes a universal mandrel which can be mounted for rotation either within a chuck or upon an arbor. The mandrel includes a wheel anchor station which allows quick axial fitting and removal of a disposable polishing wheel.

7 Claims, 1 Drawing Sheet

DENTAL MANDREL/POLISHING-WHEEL SYSTEM

BACKGROUND AND SUMMARY OF THE INVENTION

This invention pertains to dental polishing, and more particularly, to a unique polishing-wheel/mandrel system which minimizes the possibility of cross contamination from patient-to-patient, or from patient-to-health-care-provider, or vice versa.

In recent years, the concern in dental offices about what might be thought of as person-to-person hygiene has mounted significantly. Accordingly, in various aspects of dental practice, new procedures and systems are being implemented and installed to minimize, as much as possible, the likelihood of person-to-person cross contamination.

One of the areas in which such a concern has existed involves the usual polishing-wheel station wherein various within-the-mouth appliances, such as dentures, are polished. In the past, it has been typical practice for a polishing wheel in this station to be used repeatedly in connection with the work done for many different patients, until the wheel is worn to a point where it must be replaced. Obviously, this kind of practice opens the door for possible cross contamination.

In this setting, a general and significant object of the present invention is to provide a unique polishing-wheel/mandrel system in which a polishing wheel is used for the work of only one patient, and then discarded for replacement with another wheel which will be used for the next patient.

Another object of the invention is to provide such a system in which successive wheels are easily and quickly installed and replaced.

Still another object of the invention is to provide such a system which includes a wheel-supporting mandrel that is universalized in the sense that it can be mounted for rotation selectively either upon the usual quick-release lathe chuck, or drive arbor, which are found in most dental offices.

According to a preferred embodiment of the invention, the polishing wheel that is proposed is formed of a suitable, stiff, foam-like substance, such as a conventional, closed-cell, polyethylene foam material. Such material is extremely easy to work with, and low enough in expense to promote one-use-only disposability. The support mandrel for the wheel, which mandrel is easily sterilized between uses for successive patients, includes a central wheel anchoring station that allows for quick axial fitting and removal of a wheel. A wheel mounted in this station is prevented from rotation relative to the mandrel by axially extending prongs which puncture and penetrate a wheel mounted in the station.

In a modified form of the invention, and especially to accommodate special situations involving significant lateral (axially directed) polishing forces, a reversible, attachable/detachable, and reusable, retainer ring is employed.

These and other objects and advantages which are obtained by the invention will become more fully apparent as the description that now follows is read in connection with the accompanying drawings.

Figure 4:
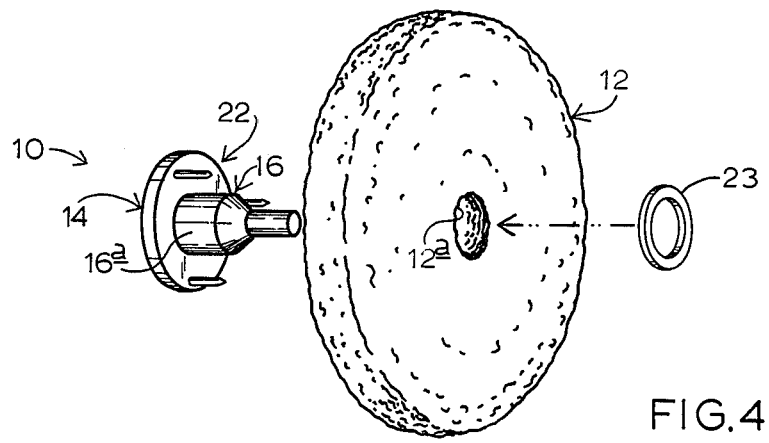
FIG. 4, which is drawn on a smaller scale than that used in FIGS. 1, 2 and 3, shows the mandrel of the present system in a position spaced from and about to receive a polishing wheel according to the invention.

In addition, and in order to conserve drawing space, the right-hand side of FIG. 4 is used to illustrate a modification wherein a lateral-force retainer ring is employed for the wheel.

Figure 5:
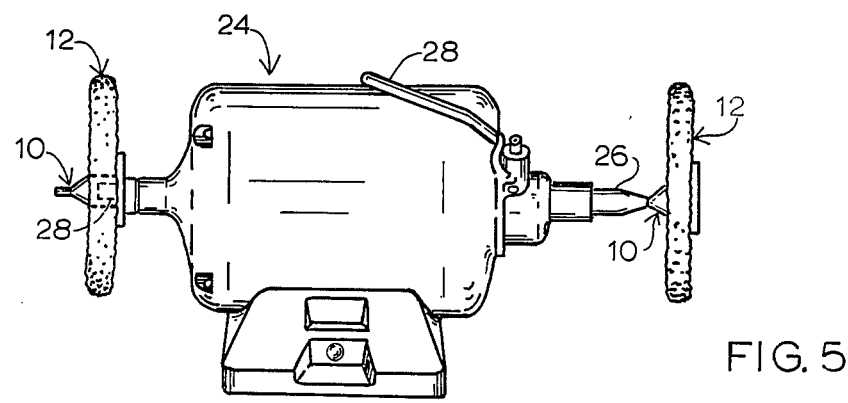

FIG. 5 is a view on an even smaller scale than that used in FIG. 4, showing a conventional dental lathe, and illustrating the universal mounting capability of the system.

DETAILED DESCRIPTION OF THE INVENTION

Turning attention now to the drawings, and referring first of all to FIGS. 1-4, inclusive, the system of the invention includes a wheel-support mandrel 10 which is usable, seriatim, with hygiene-promoting, single-use-only polishing wheels, such as the one shown at 12 in FIG. 4.

Figure 1:
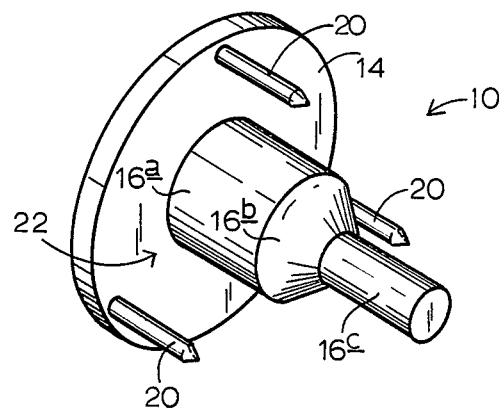
FIG. 1 is a perspective view of a polishing-wheel support mandrel that forms part of the system proposed by the present invention.
Figure 2:
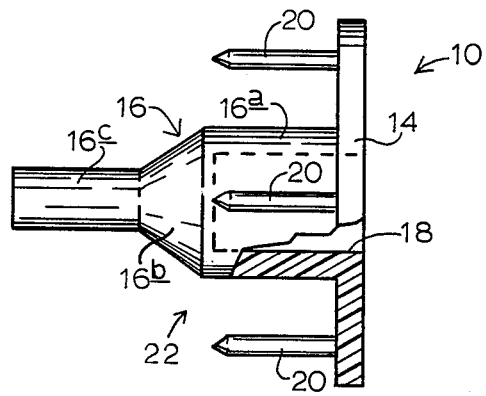
FIG. 2 is a side view of the mandrel of FIG. 1, with a portion broken away to illustrate details of construction.
Figure 3:
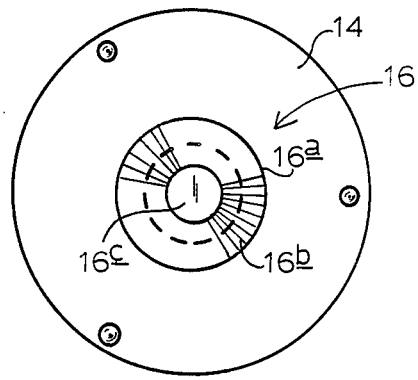
FIG. 3 is a view taken from the left side of FIG. 2.

Mandrel 10, which preferably is formed as a unitary structure from a suitable molded plastic material, includes a main annular support flange 14 from one side of which extends a stepped-diameter projection 16, including a large-diameter portion 16a which joins through a frustroconical portion 16b with a small-diameter portion 16c. As can be seen in FIG. 2, extending axially centrally through flange 14 and into projection portion 16a is a bore, or socket, 18.

Extending axially from near the perimeter of flange 14, in the same direction as projection 16, are three prongs 20, which are also referred to herein as anti-slip means. Prongs 20 along with projection portion 16a, which is also referred to herein as a support hub, together define a wheel anchor station generally designated 22.

Mandrel 10 offers what is referred to herein as a universal (bidirectional) mounting capability, inasmuch as its projection portion 16c is adapted for reception within a conventional chuck in the usual dental lathe, and its socket 18, which is slightly tapered, is adapted for press fitment on the usual drive arbor in such a lathe. Accordingly, this projection portion and socket are appropriately sized to fit the recognized size standards associated with such a lathe.

The kind of polishing wheel which is proposed for the system of the invention, such as wheel 12, is preferably formed of a relatively stiff, closed-cell foam material. While various materials can be used for this purpose, the one which we have mentioned above is very adequate for the purpose. Wheel 12 is formed with a central aperture 12a which offers a clearance fit with the outside of hub 16a.

It should be apparent that the system proposed by the invention allows for quick axial fitting and removal of wheels, one after another, as they are used on a single-patient-only basis, with mounting being accomplished simply by pressing the wheel axially onto the hub with prongs 20 penetrating and thus gripping the wheel. These prongs, of course, prevent the wheel from rotating relative to the mandrel during a work procedure. Obviously, removal and replacement of wheels is an extremely simple procedure.

As was mentioned earlier, a modified form of the invention is proposed for situations, special situations, that involves significant lateral (axially directed) polishing forces. More particularly, and this modification is illustrated at the right-hand side of FIG. 4, what is proposed for inclusion in the system is a reversibly attachable/detachable lateral-force retainer ring 23 which preferably is formed of a suitable, sterilizable elastomeric material. In situations where it is desired to employ such a ring, after a polishing wheel is mounted on hub 16a, the ring, designed to have a press fit with the hub, is pressed onto the same. Following use, this ring is removed to allow easy removal of the wheel.

While, ordinarily, we would have provided a separate, stand-alone drawing to illustrate this modification, the technique chosen herein—combining it in FIG. 4—was chosen to conserve drawing space.

At 24 in FIG. 5, there is shown a conventional, double-ended dental lathe, at the right end, or side, of which there is a conventional quick-release chuck 26 which is opened and closed by manipulation of a lever 28, and at the left end, or side, of which in FIG. 5 there is a drive arbor 30. In order to illustrate the universal mounting capability of the system, two systems are shown mounted on lathe 24. More specifically, the system which is at the left side of the lathe in FIG. 5 is mounted on arbor 30, and that on the right side of FIG. 5 is mounted within the jaws of chuck 26.

The system is readied for use by sterilizing mandrel 10, and by then mounting on it a new (yet unused) polishing wheel 12. The assembled system is then mounted as desired on a dental lathe and employed for whatever is the intended purpose.

When that work is complete, the system is removed from the lathe, the used wheel discarded, and the mandrel sterilized in preparation for the next use.

Thus, and from the description which has just been given, the important features and advantages offered by the invention in promoting dental office hygiene should be readily apparent. And, while certain materials have been expressed above as being preferable materials in the construction of the system, certainly other suitable materials, where desired, may be used.

Thus, while a preferred embodiment, and a modification, of the invention have been described herein, it is appreciated that other variations and modifications may be made without departing from the spirit of the invention.

It is claimed and desired to secure by Letters Patent:

1. A hygiene-promoting, universal, quick attach/detach, rotary dental polishing-wheel/mandrel system comprising
    a bidirectionally mountable, polishing-wheel support mandrel including means enabling attachment thereof both to a rotary chuck and to a rotary arbor, and an axial-motion-accommodating anchor station for such a wheel, and
    a single-patient-only-committed, disposable polishing wheel axially fittable within and removable from said station.

2. The system of claim 1, wherein said wheel is formed of a stiff foam-like substance.

3. The system of claim 1, wherein said station includes an elongate central support hub, and anti-slip means for securing a wheel fitted in said station against rotation relative to said mandrel.

4. The system of claim 3, wherein said anti-slip means includes at least one axially extending prong adapted to penetrate a wheel fitted in said station.

5. The system of claim 1, wherein said mandrel is elongate, and includes, adjacent one end, a projection fittable within a chuck, and adjacent the other end, a socket adapted to receive an arbor.

6. The system of claim 1 which further includes a lateral-force retainer reversibly replaceable on said wheel support mandrel for offering lateral support for a wheel fitted within said station.

7. The system of claim 6, wherein said retainer takes the form of a reusable ring which is press fittable on said mandrel.

* * * * *